United States Patent [19]

Martel et al.

[11] Patent Number: 4,883,493
[45] Date of Patent: Nov. 28, 1989

[54] LEG PROSTHESIS

[76] Inventors: Guy G. Martel, 350 The Driveway, Apt. #1205, Ottawa, Ontario, Canada, K1S 3N1; Edwin A. Iler, 32 Gray Court Drive, Ancaster, Ontario, Canada, L9G 2S1

[21] Appl. No.: 181,609

[22] Filed: Apr. 13, 1988

Related U.S. Application Data

[63] Continuation of Ser. No. 802,911, Nov. 29, 1985, abandoned.

[51] Int. Cl.⁴ .............................................. A61F 2/80
[52] U.S. Cl. ........................................ 623/38; 623/46
[58] Field of Search ................................... 623/27–32, 623/38–46; 135/68, 69, 82

[56] References Cited

U.S. PATENT DOCUMENTS

| | | | |
|---|---|---|---|
| 2,478,667 | 8/1949 | Shellhouse | 135/68 |
| 2,859,451 | 11/1958 | Mauch | 623/39 |
| 3,889,301 | 6/1975 | Bonner | 623/38 |
| 4,051,558 | 1/1977 | Valloton | 623/43 |
| 4,215,441 | 8/1980 | Wilson | 623/44 |
| 4,370,761 | 2/1983 | Serri | 623/43 |
| 4,619,660 | 10/1986 | Christiansen | 623/46 |

FOREIGN PATENT DOCUMENTS

| | | | |
|---|---|---|---|
| 0168889 | 9/1951 | Fed. Rep. of Germany | 623/44 |
| 1074522 | 2/1984 | U.S.S.R. | 623/44 |

OTHER PUBLICATIONS

Daw Industries Brochure on "Four Bar Pneumatic Knee".

Primary Examiner—Richard J. Apley
Assistant Examiner—James Prizant
Attorney, Agent, or Firm—Rogers & Scott

[57] ABSTRACT

A leg prosthesis is disclosed which incorporates a novel spring-biased telescopic shank permitting amputees to run and take part in a variety of sports such as volleyball and basketball. The shank includes a spring and damper piston which absorb ground impact forces shortening the shank at heel-strike minimizing the impact on the amputee's stump. At toe-off the spring recoils to restore the original length of the limb and provides impetus to accelerate the prosthetic leg so that full extension of the leg occurs prior to the next heel-strike. The shank can be prestressed for use with amputees of different weight and can be readily fitted to conventional prosthetic feet and knees.

8 Claims, 3 Drawing Sheets

LEG PROSTHESIS

This application is a continuation of application Ser. No. 802,911 filed 11/29/85 abandoned.

The present invention relates to a limb prosthesis and particularly, but not exclusively, to an above knee leg prosthesis.

Loss of a limb used to mean termination of a sporting career or extremely limited participation in sports and athletics. However, the social acceptance and involvement of disabled athletes is becoming increasingly widespread in a variety of fields and in particular athletics. Because of this, greater demands are being placed on prostheses to withstand more extreme stresses and strains. Disabled athletes and sportsmen are keen to compete with other similarly handicapped persons in a variety of events.

Prostheses are ideally designed to duplicate the appearances and functions of the natural limbs they replace. Because this is very dfficult in practice there has to be a trade off between cosmesis and function. No prosthesis has yet been designed which permits the range of movement of a natural limb or all the functions performed by that limb.

The present invention is concerned with leg prostheses which are designed for use not only in the walking mode but also in a running mode.

The biomechanics of locomotion in walking and running are completely different. During walking both feet have simultaneous ground contact as the legs alternate from stance to swing, but during running this leg double suppot phase does not occur and the stride is a phase in which both legs are simultaneously out of contact with the ground. Heel contact in walking occurs in front of the body's center of gravity and heel contact during running occurs almost directly beneath the center of gravity. In addition, during running, step length increases and increased hip and knee flexion occur. This angle of increase in joint flexion helps to cushion the ground impact at heel contact and decreases energy expenditure by decreasing the progressive vertical displacement of the center of gravity. The flexion position also increases the knee flexion movement which results from the ground reaction force. The forward body momentum, combined with weight bearing and forceful muscle action, will overcome the increased knee flexion movement. Therefore to achieve and retain running speed, intensified muscle work and body posture reinforce existing forward momentum.

With a conventional above knee walking prosthesis it is very difficult for an amputee to run. For example, Terry Fox ran half way across Canada with an above-knee prosthesis which was a modified walking prosthesis. This prosthesis was inherently unsuitable for running and extension of the prosthesis during the swing phase was often incomplete so that Terry Fox had to sway laterally and simultaneously hop using his other leg to allow enough time for the prosthesis to swing through to reach heel contact and to accomodate the forward momentum of his body at running speed. This extra "hop skip" also decreases the distance from his own foot to the prosthetic foot prior to the prosthetic heel contact and this results in reduced reflex movement on the prosthetic side making it possible for the amputee to maintain prosthetic knee control as the body rises and moves forward. This extra hop and walking action is very exhausting because it results in a double stance phase on the same side. Not only this, but because of the swaying movement which is very unnatural, this places considerable strain on the spine and back muscles. Because the amputee must fully extend the prosthetic knee to ensure stance stability the running pattern is abrupt and the stump experiences an impact with each prosthetic step. This impact can result in severe forces being set up between the socket and the stump and can be very painful. Thus the hop skip is the body's way of minimising the stump socket stress. This pattern is in contrast to that of bipedal running during which the natural knee remains flexed when the weight is carried over the stance leg. However with present prosthetic knees which flex to a degree needed for running, the knees cannot simultaneously support the body and provide stance stability.

Terry Fox attempted to overcome this problem by attaching a very strong elastic strap between the shank of the prosthesis and the stump socket to attempt to pull the shank forward during the swing phase so that it would be ready for heel strike. However, this was only a marginal improvement and during running Terry Fox still swayed considerably which, as mentioned above, was very exhausting.

A prosthetic limb suitable for running as well as walking should satisfy a number of design criteria in addition to being easy to construct and also being inexpensive. For example, it should be comfortable, it should prevent internal and external stump rotation which may occur during running. It should also provide sufficient extension so that the hip joint during the swing phase can provide full extension of the leg even during fast running so that the artificial foot can be correctly located for heel strike and at the same time provide stance stability. The prosthetic limb should also be easy to assemble and use easily available components and should be capable of being readily fitted by a prosthetist. Also the limb should minimise the stresses set up between the stump and the socket during running so that the tendency for the runner to hop skip on his own foot is obviated and the locomotion is very similar to normal bipedal running.

It is an object of the present invention to provide an improved leg prosthesis which permits more active amputees having one natural leg to run. This is provided by incorporating a telescopic portion in the prosthesis to allow a change in length when the amputee's weight is carried on the prosthesis so that in a running mode the amputee can move his natural leg forwardly past the prosthesis without elevating his centre of gravity significantly. Energy stored in the prosthesis is then used to assist forward motion as the weight is transferred to the natural leg.

This and other aspects of the invention will become apparent from the following description when taken in combination with the accompanying drawings in which.

Figure 1:
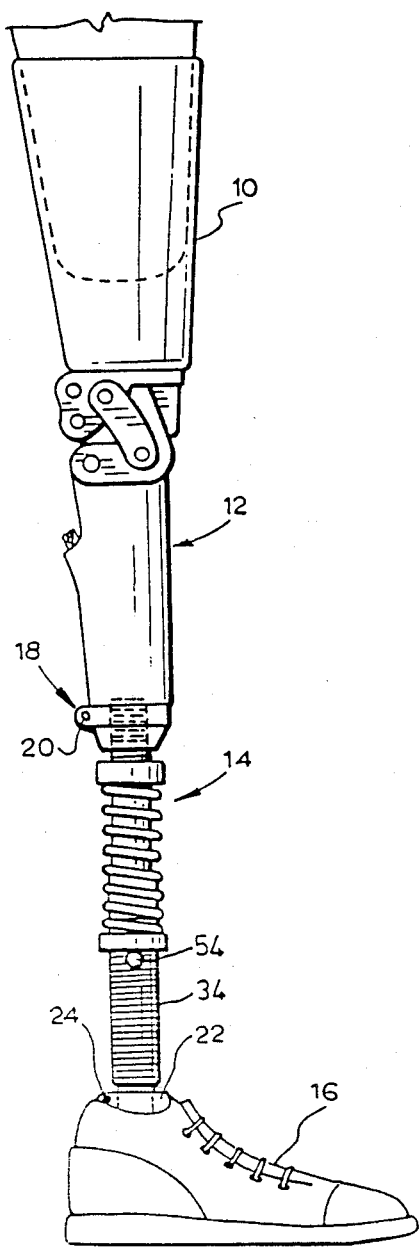
FIG. 1 is a diagrammatic view of a prosthetic above-knee limb illustrating a telescopic shank portion.

Reference is firstly made to FIG. 1 of the drawings which shows a prosthetic leg in accordance with a preferred embodiment. The leg consists of a stump socket 10 coupled to a Teh-Lin (trade mark) knee prosthesis 12 (DAW Industries Inc., Minn., U.S.A.) and a spring-loaded shank, generally indicated by reference numeral 14, the bottom of which is connected to an artificial foot 16.

The Teh-Lin knee prosthesis is a commercially available product which permits flexion and extension of the shank 14 relative to the stump socket during walking and running and which locks in both a flexed and unflexed configuration so that the amputee is enabled to support weight on the prosthesis in either configuration. Further, the Teh Lin (TM) prosthetic knee can move freely between the flexed and unflexed configurations by a simple shift in weight of the amputee.

The Teh Lin (TM) prosthetic knee includes a socket attachment at the top, a joint intermediate the ends of the knee comprising a four bar over centre parallel lever arrangement, and a spring biased pneumatic unit located below the joint for controlling flexibility and extension of the joint. The pneumatic unit is encased in a shaft which is split at its lower end 18 to receive the shank 14 and has a pin 20 to secure the shank 14 in the shaft. The bottom of the shank fits into a split shaft 22 located in the foot and is secured by pin 24 in the same manner.

Figure 2:
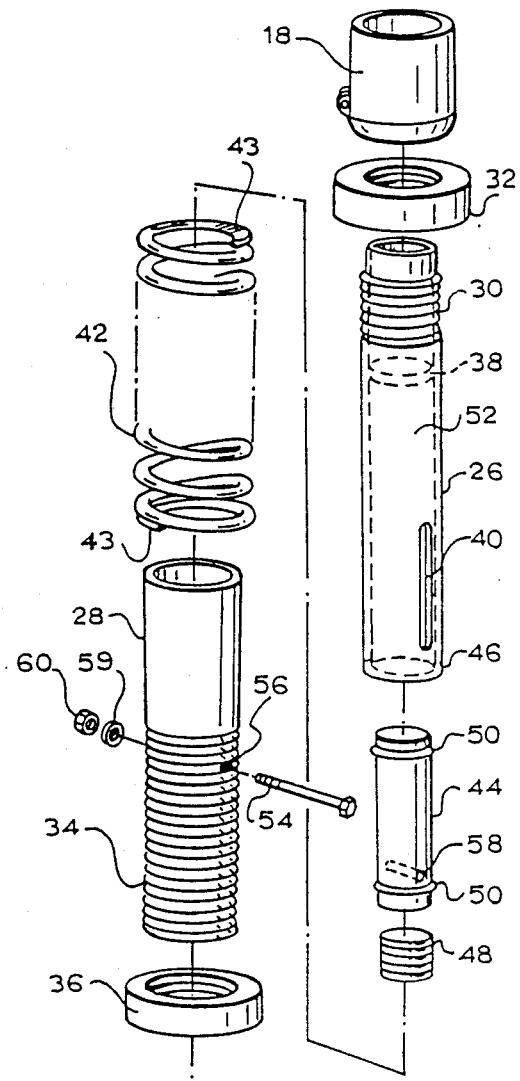
FIG. 2 is an enlarged and exploded view of a part of the telescopic shank assembly.

Reference is now made to FIG. 2 which is an enlarged and exploded view of parts of the shank 14. Basically, the shank consists of a hollow inner shaft 26 and a hollow outer shaft 28 which are coupled to portion 18 of the Teh-Lin knee prosthesis 12 and to the foot 16 respectively. The inner shaft 26 has a threaded top portion 30 for receiving a threaded collar 32, and the outer shaft has a threaded bottom portion 34 for a receiving collar 36. The inner shaft 26 contains a transverse web 38 and has opposed longitudinally extending slots 40 (one of which is shown) in the shaft wall.

A heavy duty coil spring 42 is mounted between collars 32, 36 for providing resilience to permit running action as will be described. The spring has flattened end coils 43 to provide even pressure on the collars 32, 36. A damper piston 44 is provided for location within the inner shaft 26 to dampen the relative movement between the shafts and to absorb impact resulting from contact between the foot 16 and the ground to relieve impact forces on the stump. The inner shaft 26 has its lower end 46 internally threaded to receive a plug 48 having complementary threads and adapted to retain the piston 44 within the shaft and the piston 44 has spaced 0-rings 50 for closely engaging the interior of inner shaft 26. The 0-rings seal the upper portion 52 of the hollow inner shaft 26 so that during walking or running air located between the top of the piston 44 and web 38 is compressed to provide damping of the walking or running forces. Two spaced 0-rings are used to centre the piston 44 in the shaft and minimize wear and maximize damping efficiency.

The shank 14 is assembled as follows. Firstly, collars 32, 36 are fitted onto shafts 26, 28 respectively at a predetermined distance apart which is determined by the patient's weight. Piston 44 is mounted in inner shaft 26 and plug 48 secures the piston therein. The spring 42 is then fitted over shaft 28 to be supported by the collar 36 and shaft 26 with the piston located within the shaft 26. The shafts are positioned so that coupling bolt 54 passes through aperture 56 (one of which is shown) through slots 40 and through a drilled hole 58 in the piston to couple the shafts together. The bolt is retained by a nut 60 on a washer 59.

The shafts 26 and 28 are forced together against the force of spring 42 so that the coil spring is compressed by a predetermined amount corresponding to the weight of the patient. The collars 32, 36 are adjusted to hold the spring at this compression and the shank is then coupled to the Teh-Lin knee prosthesis and foot.

Figure 3:
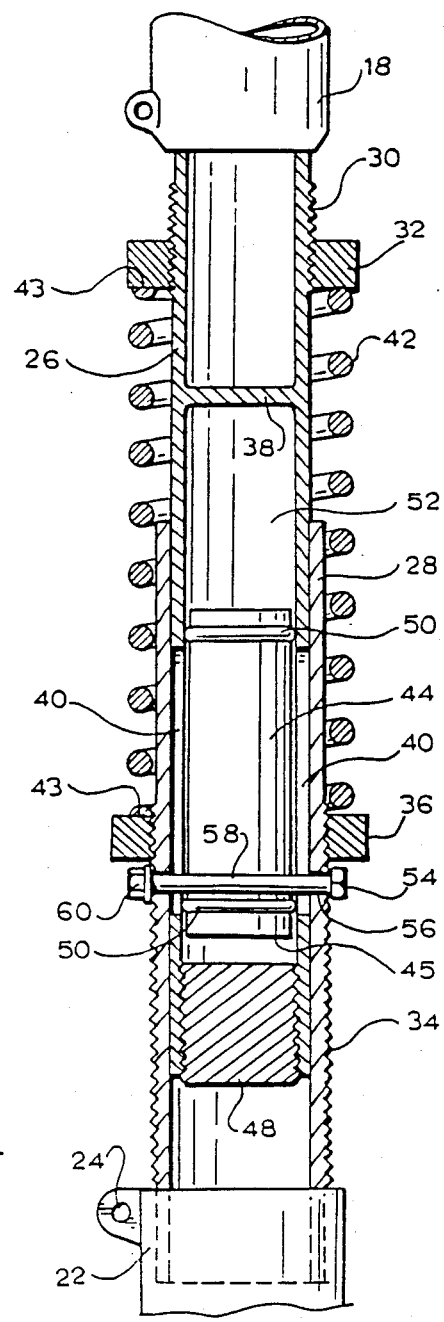
FIG. 3 is an enlarged view of a section through an assembled telescopic shank assembly in a fully extended position.

The assembled shank is shown in enlarged cross-section in FIG. 3. The piston 44 is positioned with shaft 26 such that top 0-ring 50 is disposed above the top of slots 40 and the bolt 54 is located just above the bottom of slots 40. There is also clearance between the bottom 45 of piston 44 and the top of the plug 48 for reasons described below.

Figure 4A:
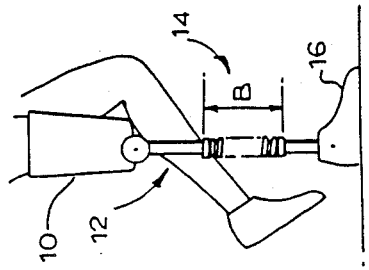
FIGS. 4a, 4b, 4c and 4d illustrate the extension of the telescopic shank at various stance phases during running.
Figure 4B:
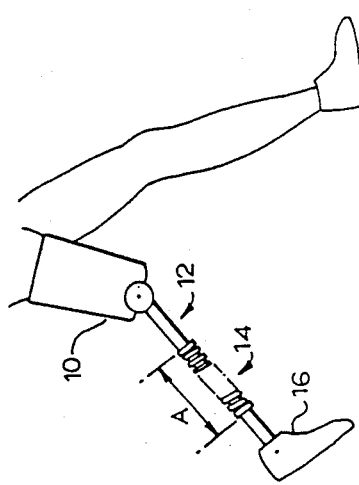
Figure 4C:
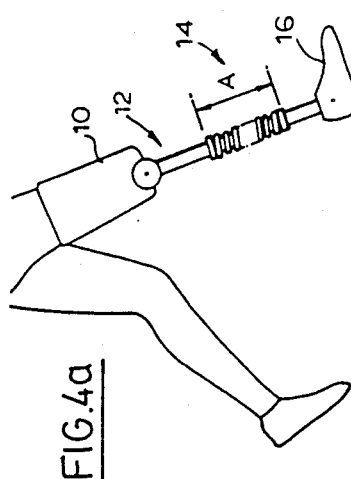

Reference is now made to FIGS. 4a to 4d as well as FIG. 3. It will be appreciated that the knee-joint is shown diagrammatically for ease of illustration. During running a stride begins at heel-strike as shown in FIG. 4a. In the position just before heel-strike the spring is fully extended so that the distance between collars 32, 36 shown as "A", is the distance also shown in FIG. 3. As the amputee transfers momentum and weight onto foot 16 the heel impact causes outer shaft 28 to move relative to inner shaft 26 thereby compressing spring 42 as shown by distance "B" in FIG. 4b and shortening the leg overall. When this occurs the spring is compressed and the piston 44 is forced upwardly into space 52. Because the air is sealed between web 38 and upper 0-ring 50, the air is compressed and assists the spring in reducing the impact loading on the stump located in the socket 10. The result is to reduce the length of the shank to allow the amputee to bring his body weight over the prosthesis with the knee extended (FIG. 4b) without having to raise his centre of gravity significantly at mid-stride. As the natural leg is slung forwardly towards the FIG. 4c position, weight on the artificial limb is relieved and the spring and air forces begin to restore the shank towards its original length. Also, as the prosthesis is moved into the FIG. 4c position, the potential energy due to spring and air compression on loading is recovered to assist in expanding the prosthesis and propelling the amputee at toe-off.

Further the spring returns to its length "A" friction between 0-rings 50 and interior of shaft 26 prevents sudden jarring movement. As the speed of running increases and the transient impact load on the spring increases the spring restoring time also decreases so that full extension always occurs before the next heel strike.

Figure 4D:
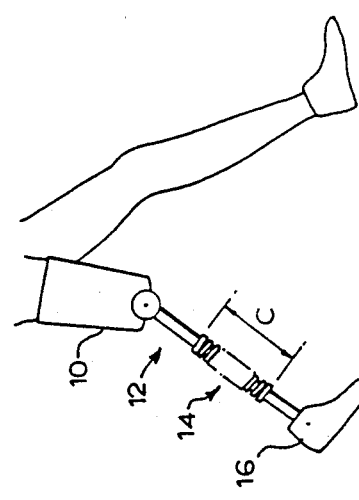

When the toe-off phase of the stride occurs as shown in FIG. 4d the spring is restored to its prestressed length "A". When in this position, the clearance between the bottom of the piston 44 and the top of the plug 48 contains a cushion of air and clearance between bolt 54 and bottom of the slots 40 is such that contact is avoided which otherwise could greatly shorten the life of the parts and affect efficient operation of the shank. The restoring spring force is such that the presthetic leg is at full extension in time for the next heel-strike as shown in FIG. 4a.

Also, during running, compression of the spring and heel damper contributes to a quicker flat foot position and hence stability. Spring compression combined with forward momentum decreases the knee flexion movement produced by the ground reaction force and, as indicated above, a spring restoring force assists toe-off which results in body acceleration and pelvic forward thrust. This helps to raise the amputee's centre of gravity to a maximum during mid-stride on the natural leg, thereby reducing the muscle work of that leg.

To begin running, the amputee uses trunk flexion and a modified spring start to push from the natural leg while the prosthetic leg is slightly abducted, which provides a broader stance base and permits the prosthesis to act as a lever facilitating spinal rotation that helps the amputee gain speed. When running speed is attained, the trunk is upright and similar to the normal jogging posture. Spinal rotation is less than in "normal" running and it has been observed that the shoulder on the sound side rises at the same time as the spring is recoiling, assisting in propelling the prosthesis into the swing phase.

In addition to running, the prosthesis permits stride-jumping and continuous hopping on the prosthesis, both of which are impossible on standard prostheses. This permits the amputee to participate in a wide range of hitherto "off-limit" sports such as volleyball and basketball.

It will be appreciated that various modifications may be made to the structure hereinbefore described. For example, the coil spring could be replaced by a resilient rubber sleeve and the damper piston could be omitted although less damping would then occur. Also the bottom shaft could be the outer shaft. Two or more spring-loaded shanks could be placed in parallel and coupled to the foot and knee. Damping may also be provided by means other than a piston, for example hydraulic fluid or counter-acting springs. It will also be appreciated that the telescopic shank could be fitted to a below-knee prosthesis. The parts may be made of any materials which have the required strength and weight to permit ease of use.

An advantage of this invention is that the amputee can take part in a a wide variety of sports. Full extension of the leg occurs permitting true running and minimizes spinal rotation and lateral sway during running. The structure is straight-forward and requires minimal parts and can be preloaded to meet the requirements of amputees with a variety of different body weights.

We claim:

1. A running prosthesis for use by a leg amputee amputated below the knee and having a leg stump and a natural leg, the prosthesis comprising:
    attachment means for connecting the prosthesis to said stump;
    a shank having upper and lower ends and being coupled at said upper end to the attachment means;
    a foot for engagement with the ground and coupled to said lower end of the shank; and
    said shank comprising a first part defining said upper end and a second part telescopically engaged with the first part and defining said lower end, resilient means engaged between said parts to bias the parts away from one another and into a relationship corresponding to the full length of the prosthesis whenever the prosthesis does not support the amputee, the resilient means being responsive to end loading in the shank to allow the first and second parts to move relative to one another to reduce the length of the prosthesis and so store potential energy in the prosthesis so that during running movements when the amputee is supported by the prosthesis the amputee can move his natural leg forwardly past the prosthesis with minimal vertical movement of the amputee's centre of gravity, the amputee further being propelled upwardly and forwardly as the weight of the amputee is transferred from the prosthesis to his natural leg and the potential energy stored in the prosthesis is released.

2. A prosthesis as claimed in claim 1 in which the resilient means is a coil spring.

3. A prosthesis as claimed in claim 1 in which the resilient means is a combination of a coil spring and air compression means.

4. A prosthesis as claimed in claim 3 in which the compression means includes a piston attached to one of the upper and lower parts and slidable in the other of the upper and lower parts to trap air to provide said air compression means.

5. A running prosthesis for use by a leg amputee amputated above the knee and having a leg stump and a natural leg, the prosthesis comprising:
    attachment means for connecting the prosthesis to said stump;
    a knee joint connected to the attachment means;
    a shank having upper and lower ends and being coupled at said upper end to the knee joint;
    foot for engagement with the ground and coupled to said lower end of the shank; and
    said shank comprising a first part defining said upper end and a second part telescopically engaged with the first part and defining said lower end, resilient means engaged between said parts to bias the parts away from one another and into a relationship corresponding to the full length of the prosthesis whenever the prosthesis does not support the amputee, the resilient means being responsive to end loading in the shank to allow the first and second parts to move relative to one another to reduce the length of the prosthesis and so store potential energy in the prosthesis so that during running movements when the amputee is supported by the prosthesis, the amputee can move his natural leg forwardly past the prosthesis with minimal vertical movement of the amputee's centre of gravity, the amputee further being propelled upwardly and forwardly as the weight of the amputee is transferred from the prosthesis to his natural leg and the potential energy stored in the prosthesis is released, the knee joint being adapted to lock and support weight in both a flexed and unflexed configuration and to move freely therebetween as the weight of the amputee is transferred from the prosthesis to the natural leg.

6. A prosthesis as claimed in claim 5 in which the resilient means is a coil spring.

7. A prosthesis as claimed in claim 5 in which the resilient means is a combination of a coil spring and air compression means.

8. A prosthesis as claimed in claim 7 in which the compression means includes a piston attached to one of the upper and lower parts and slidable in the other of the upper and lower parts to trap air to provide said air compression means.

* * * * *